United States Patent [19]

Ogawa

[11] Patent Number: 5,212,094
[45] Date of Patent: May 18, 1993

[54] AUTOMATIC CHEMICAL ANALYZER

[75] Inventor: Yoshifumi Ogawa, Ootawara, Japan

[73] Assignee: Kabushiki Kaisha Toshiba, Kawasaki, Japan

[21] Appl. No.: 687,096

[22] Filed: Apr. 19, 1991

Related U.S. Application Data

[63] Continuation of Ser. No. 537,794, Jun. 14, 1990, abandoned, which is a continuation of Ser. No. 95,631, Sep. 14, 1987, abandoned.

[30] Foreign Application Priority Data

Sep. 16, 1986 [JP] Japan .................. 61-218695

[51] Int. Cl.$^5$ .......................................... G01N 35/02
[52] U.S. Cl. ............................................. 436/47; 422/64
[58] Field of Search .................................. 422/63–67; 436/47–49

[56] References Cited

U.S. PATENT DOCUMENTS

| | | | |
|---|---|---|---|
| 4,311,394 | 1/1982 | Manabe | 422/64 |
| 4,313,735 | 2/1982 | Yamashita et al. | 422/64 |
| 4,459,265 | 7/1984 | Berglund | 422/64 |
| 4,629,703 | 12/1986 | Uffenheimer | 422/64 |
| 4,785,407 | 11/1988 | Sakagami | 422/64 |

Primary Examiner—Jill A. Johnston
Attorney, Agent, or Firm—Oblon, Spivak, McClelland, Maier & Neustadt

[57] ABSTRACT

An automatic chemical analyzer uses an odd number of reaction tubes, for example, 13 tubes. These reaction tubes are arranged at regular intervals along a circular arrangement line, on a ring-shaped holder which is disposed on a rotating table. Samples and reagents are respectively dispensed into the reaction tubes when they are at a sample dispensing position and at a reagent dispensing position both situated on the arrangement line. The rotating table is driven so that the reaction tubes move intermittently along the arrangement line. If the interval between each two adjacent reaction tubes is designated as one pitch, the tubes are moved substantially half round the arrangement line, e.g., for seven pitches, in each cycle. While the reaction tubes move for such a distance, liquid mixtures of the samples and reagents therein are subjected to photometry. After undergoing a predetermined photometric process, the reaction tubes are washed. Thus, the time required for the movement of the reaction tubes in each cycle can be shortened. Moreover, those reaction tubes which require washing can be situated collectively in a specified position.

2 Claims, 7 Drawing Sheets

AUTOMATIC CHEMICAL ANALYZER

This is a continuation of application Ser. No. 07/537,794, filed on Jun. 14, 1990, and now abandoned, which in turn is a continuation of application Ser. No. 07/095,631, filed on Sep. 14, 1987, and now abandoned.

BACKGROUND OF THE INVENTION

The present invention relates to an automatic chemical analyzer for continuously obtaining photometric data on a plurality of reaction tubes into which samples and reagents are dispensed, while moving the reaction tubes along an endless arrangement line.

Figure 1A:
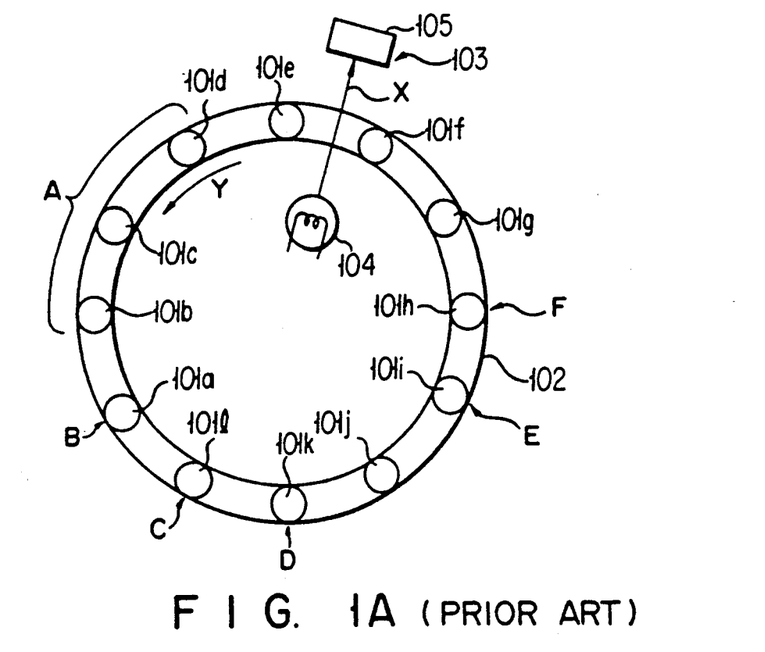
FIGS. 1A and 1B schematically illustrate a prior art automatic chemical analyzer in which reaction tubes are rotated for one revolution plus one pitch.

FIG. 1A shows an example of a conventional automatic chemical analyzer for chemically analyzing human serum and the like.

In this analyzer, a plurality of reaction tubes 101a to 101l are arranged on ring-shaped holder 102, which is arranged on a rotating table (not shown). For simplicity, the analyzer of FIG. 1A is shown as using only 12 reaction tubes 1a to 101l, although an actual analyzer would use several times this number. Tubes 101a to 101l are made of glass or other material which transmits light. As the rotating table rotates, the reaction tubes are rotated in regular cycles, in the direction indicated by arrow Y in FIG. 1A.

Ring-shaped holder 2 is surrounded by a washing unit, a sample dispensing unit, a first-reagent dispensing unit, a first stirring unit, a second-reagent dispensing unit, and a second stirring unit, none of these units being shown in FIG. 1A. Washing positions A for the washing unit, sample dispensing position B for the sample dispensing unit, first-reagent dispensing position C for the first-reagent dispensing unit, first stirring position D for the first stirring unit, second-reagent dispensing position E for the second-reagent dispensing unit, and second stirring position F for the second stirring unit are set individually at predetermined stop positions for reaction tubes 101a to 101l. In these individual positions, specified operations of the analyzer are performed viz-a-viz the reaction tubes.

In the stop state shown in FIG. 1A, reaction tubes 101b, 101c, and 101d are washed at washing positions A. Samples (e.g., serum) and reagents, dispensed into and mixed in the reaction tubes before reaching positions A, are washed away. In sample dispensing position B, a sample is dispensed to reaction tube 101a, which has been washed in the previous cycle. In first-reagent dispensing position C, a first reagent is dispensed into reaction tube 101l, into which a sample was injected when, in the previous cycle, it was at sample dispensing position B. In first stirring position D, a sample in reaction tube 101k, is stirred together with the first reagent which was injected thereto when, in the previous cycle, reaction tube 1k was at first-reagent dispensing position C. In second-reagent dispensing position E, the second reagent is dispensed into reaction tube 101i, in which, in the last cycle but one, a sample and the first reagent were stirred. In second stirring position F, a sample and the first and second reagents in reaction tube 101h, the second reagent having been injected thereinto in the previous cycle, are stirred. Numeral 103 denotes a photometric system, which includes light source 104 and light sensing element 105. Light emitted from light source 104 crosses the path of transfer of reaction tubes 101a to 101l, and is received by sensing element 105. When moving tubes 101a to 101e intercept the light emitted from source 104 toward element 105, the quantity or intensity of light transmitted through tubes 1a to 1l vary, depending on the contents of the tubes. Thus, sensing element 105 detects, as photometric data, absorbances corresponding to the quantity or intensity of light transmitted through tubes 1a to 1l.

Figure 1B:
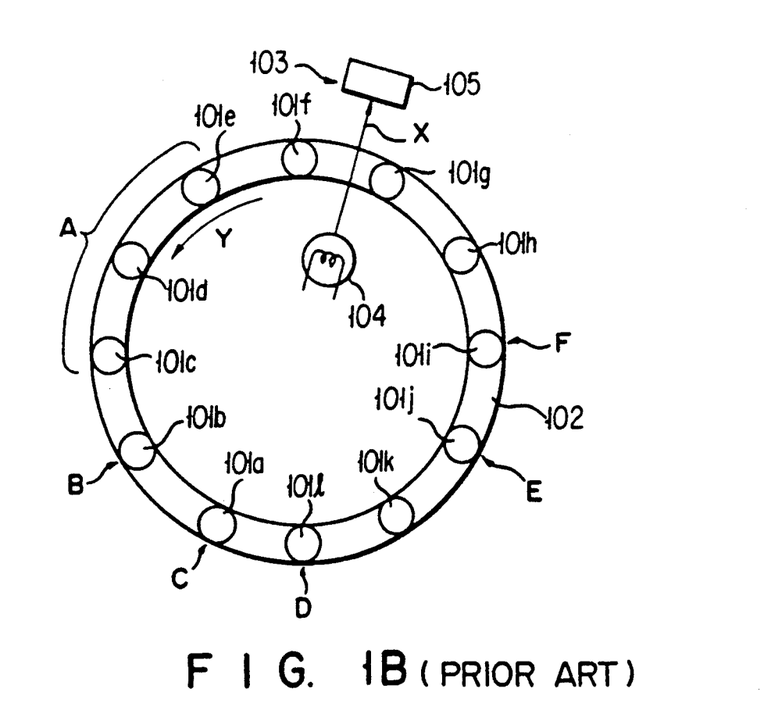

After the stationary state of reaction tubes 1a–1l shown in FIG. 1A has continued for a predetermined period of time, ring-shaped holder 102 is rotated in the direction of arrow Y for another predetermined period of time. After moving reaction tubes 1a to 1l in this manner, holder 102 is stopped again If the interval between each two adjacent reaction tubes is designated as a pitch, ring-shaped holder 102 is rotated for one revolution plus one pitch, starting from the stationary state shown in FIG. 1A. FIG. 1B shows the arrangement of reaction tubes 1a to 1l following such rotation of holder 102. In the stationary state shown in FIG. 1B, specified operations are performed for tubes 1a to 1l in their respective positions, just as in the stationary state shown in FIG. 1A.

A cycle is defined as a combination of the stop time and the time during which reaction tubes 1a to 1l move. As such a cycle is repeated, tubes 101a to 101l advance pitch by pitch. Thus, photometry can be successively performed with respect to the reaction tubes.

Figure 2A:
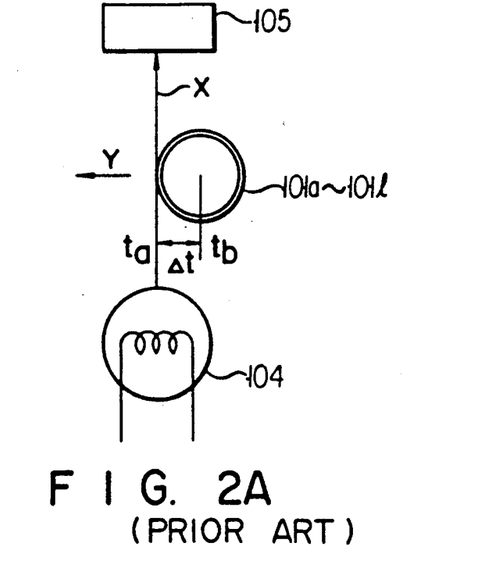
FIGS. 2A and 2B are diagrams illustrating the principle of photometry as performed by the automatic chemical analyzer.
Figure 2B:
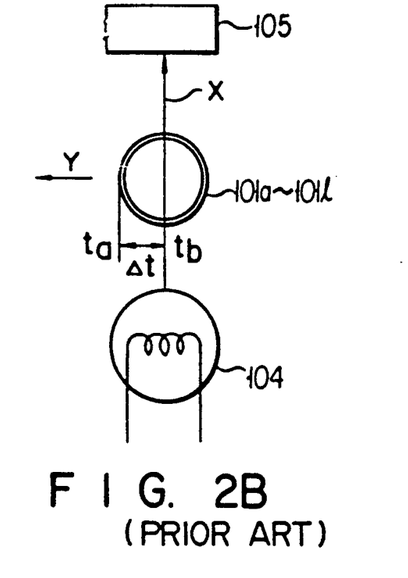

Photometric data is based on a photometric value obtained at time $t_b$, which is $\Delta t$ after time $t_a$, as shown in FIG. 2B. (At time $t_a$, optical axis X of the light from light source 104 is intercepted by any of reaction tubes 1a to 1l, as shown in FIG. 2A). Time $t_b$ is the instant when the light from light source 4 passes through the axis of each moving reaction tube.

Figure 3:
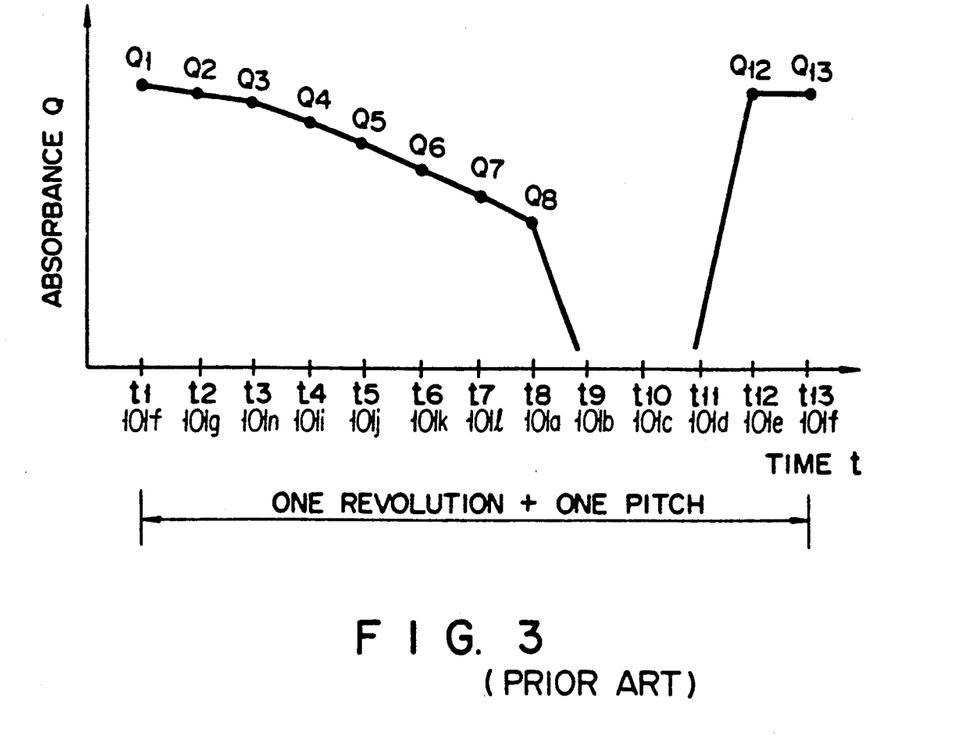
FIG. 3 shows characteristic curves obtained as a result of use of the analyzer shown in FIGS. 1A and 1B.

FIG. 3 shows photometric data obtained as a result of rotation of holder 102 from the stationary state of FIG. 1A to the stationary state of FIG. 1B, i.e., for one cycle (one revolution plus one pitch). When holder 102 starts to rotate in the direction of arrow Y, from the position of FIG. 1A, reaction tubes 101f and 101g are measured photometrically at times $t_1$ and $t_2$, respectively. After such photometric operation is repeated in succession, tube 101f is measured again at final time $t_{13}$. Thus, absorbances $Q_1$ to $Q_{13}$ of the contents of reaction tubes 1a to 1l can be obtained.

In executing the photometric operation described above, the time for each cycle is equal to the sum of the time during which the reaction tubes are rotated and the time during which holder 2 is stationary. Thus, if the rotating time and stop time are each 10 seconds, the cycle time is 20 seconds.

If, for example, the photometric processing capacity is to be increased, then the cycle time must be reduced. However, reduction of the stop time of holder 102 is restricted by various factors. Therefore, it may only be possibe to shorten the cycle time by reducing the rotating time, say from 10 seconds to 5.

If the rotating speed of holder 102 and the moving speed of reaction tubes 101a to 101l are increased at the same time, however, photometric system 103 will then be adversely affected by the resultant vibration. As a result, it becomes difficult to perform photometry at an appropriate point. Therefore, measurement errors tend to occur.

Figure 4:
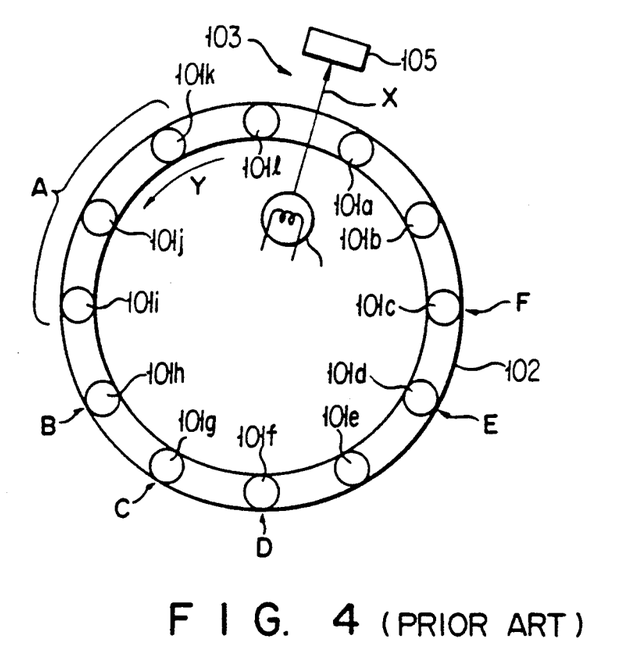
FIG. 4 is a diagram illustrating the principle of the inventor's unpublished non-prior art automatic chemical analyzer, in which reaction tubes are rotated for a half revolution plus one pitch.

With the aim of solving these problems, the present inventor is his unpublished research defined one cycle of rotation of holder 102 is defined as a half revolution plus one pitch, instead of one revolution plus one pitch, and without a change in the rotating speed (e.g., one rotation for 10 seconds) of the holder. If one cycle of rotation of holder 102 is defined as above, the cycle time can be reduced, for example from 20 seconds to 15 seconds. FIG. 4 shows the arrangement of reaction tubes 101a to 101l after the holder is rotated for a half revolution plus one pitch, starting from the stationary state shown in FIG. 1A.

In this example, the number of reaction tubes 101a to 101l is an even number (12). When holder 102 is rotated for a half revolution plus one pitch, in this case, total number P of pitches covered in each cycle is given by $P=(n/2)+1$, where n is the total number of reaction tubes 101a to 101l. Thus, the state shown in FIG. 4 is that which is in being after reaction tubes 1a to 1l are moved for 7 pitches ($P=(12/2)+1=7$), in the direction of arrow Y, starting from the stationary state shown in FIG. 1A. When the next cycle of rotation is executed, reaction tubes 101a to 101l are moved for another 7 pitches, in the same manner, and then stop.

Figure 5:
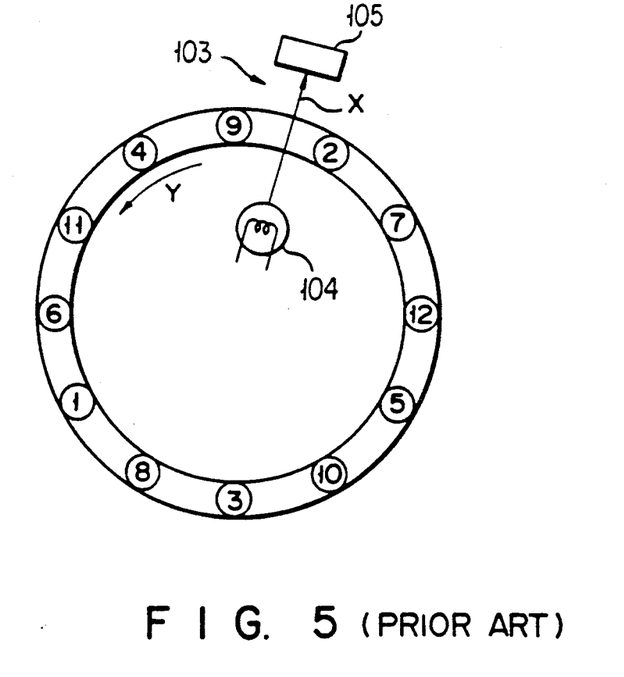
FIG. 5 is a diagram illustrating stop positions for the reaction tubes in the analyzer shown in FIG. 4.

Reaction tube 101a is observed attentively with every cycle of rotation, to follow up and determine the rotational positions to which reaction tubes 1a to 1l are moved. FIG. 5 shows the result of such observation. In FIG. 5, (1) corresponds to the stop position of reaction tube 1a as shown in FIG. 1A, and (2) indicates a stop position reached after one cycle of rotation for a 7-pitch movement. Likewise, (13) to (12) indicate stop positions reached after the following individual cycles of rotation. This result applies also to all of the 11 other reaction tubes, with the exception of the first stop position. The larger the figures indicative of the stop positions for reaction tubes 1a to 1l, the more advanced is the reaction in the reaction tubes. After the reaction is advanced to some degree, tubes 101a to 101l are washed. If the progress of the reaction is on a certain level, the last stop position (position (12) in this example) need not always be reached before the washing takes place. Thus, the time for performing washing can be determined freely, depending on the particulars of measurement.

If the arrangement of reaction tubes 101a to 101l shown in FIG. 5 is observed from such a point of view, it can be seen that the reaction tubes at positions (8) to (12), which are to be washed, for example, are situated randomly on ring-shaped holder 102. This means that washing positions A cannot then be situated collectively in specific continuous regions around holder 102. Structurally, therefore, the analyzer requires the provision of idle spaces, with the result that it cannot be as compact as desired.

Thus, in the automatic chemical analyzer of the inventor's unpublished research, reaction tubes 101a to 101l are rotated for a half revolution plus one pitch in each cycle, in order to shorten the cycle time. In this case, washing positions A cannot be situated collectively in continuous regions if the number of reaction tubes 101a to 101l is an even number. Consequently, such an analyzer cannot easily be made compact.

SUMMARY OF THE INVENTION

The object of the present invention is to provide an automatic chemical analyzer in which washing positions for the reaction tubes can be situated collectively, so that a more compact analyzer can be realized.

According to an aspect of the present invention, an automatic chemical analyzer is provided which comprises an odd number of reaction tubes, supporting means for supporting the reaction tubes at predetermined intervals along an endless arrangement line, dispensing means for dispensing a sample and a reagent, respectively, into the reaction tubes when they are at a sample dispensing position and at a reagent dispensing position each of which is situated on the endless arrangement line, drive means for driving the supporting means in a manner such that the reaction tubes move intermittently along the endless arrangement line, a first stop position for each reaction tube being situated at a distance corresponding to substantially a half revolution, along the endless arrangement line, from a second stop position next to the first stop position, photometric means for photometrically measuring a liquid mixture of the sample and the reagent in each reaction tube, while the reaction tube moves from the first stop position to the second stop position, and washing means for washing the reaction tubes which have undergone a predetermined photometric process.

According to the arrangement described above, an odd number of reaction tubes are stopped at positions at a distance corresponding to substantially a half revolution, along the endless arrangement line, from one another. Thus, the reaction tubes can be arranged substantially regularly with the progress of reaction therein, so that washing positions can be situated collectively in continuous regions.

DETAILED DESCRIPTION OF THE PREFERRED EMBODIMENT

Figure 6:
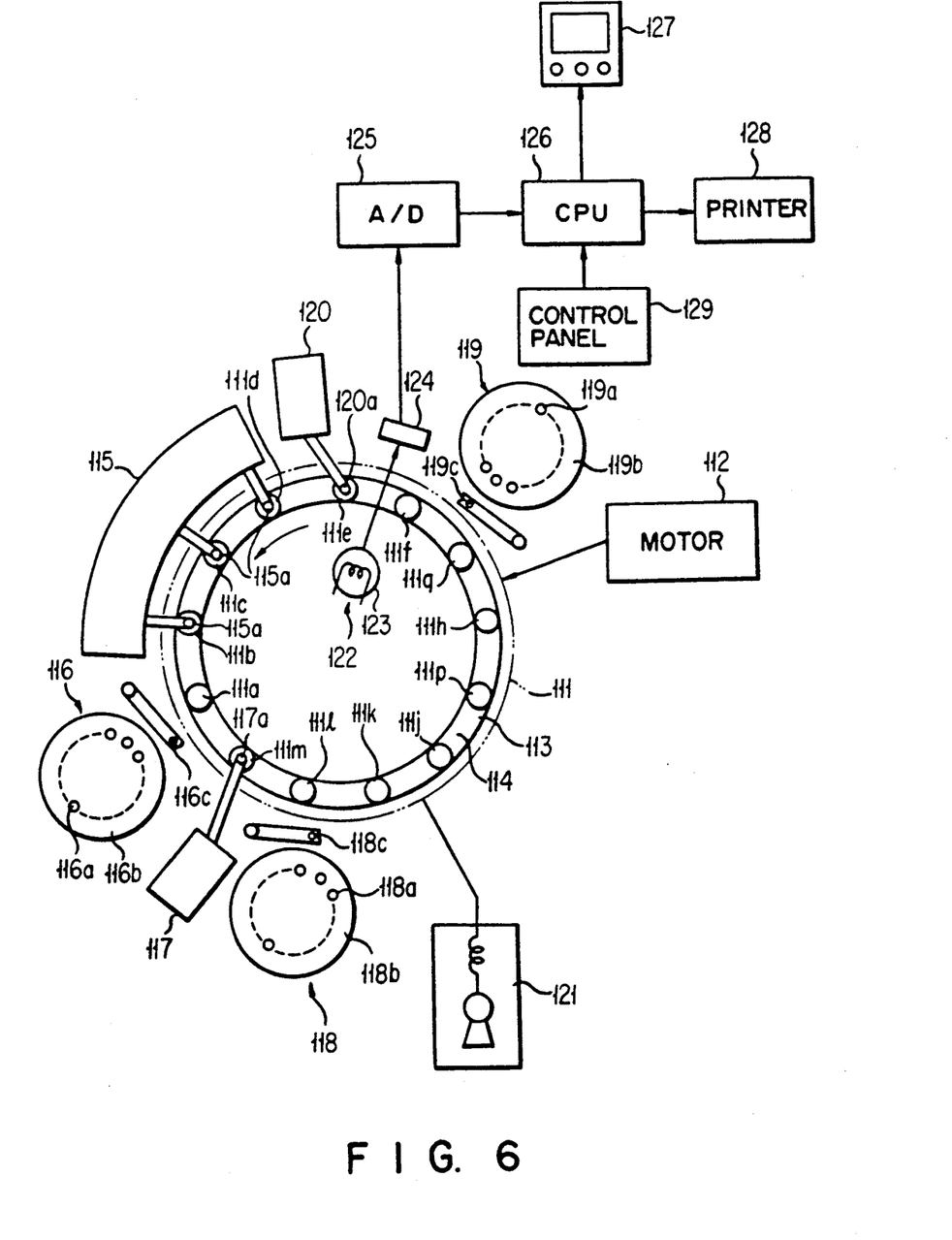
FIG. 6 is a schematic view of an automatic chemical analyzer according to an embodiment of the present invention.

In FIG. 6, numeral 111 denotes a rotating table which is rotated by means of motor 112. Ring-shaped holder 13 is provided on table 111. An odd number of reaction tubes, e.g., 13 tubes 111a to 111m, are arranged at regular intervals along circular arrangement line (endless arrangement line) 114, on holder 113. Tubes 111a to 111m are made of glass or other material which transmits light. Rotating table 111 is rotated by motor 112 so that reaction tubes 111a to 111m held on holder 113 move intermittently in regular cycles, in the direction of arrow Y of FIG. 6 along arrangement line 114.

For example, each reaction tube reaches its first stop position after moving half round circular arrangement line 114 for each cycle.

If the total number of reaction tubes 11a to 11m is odd number n, and if the interval between each two adjacent tubes is designated as a pitch, number P of pitches covered by one cycle is expressed as $(n+1)/2$. In this embodiment, total number n is $n=13$, so that we obtain $P=(13+1)/2=7$. During one cycle, therefore, reaction tubes 11a to 11m move from their respective stop positions shown in FIG. 7A to the stop positions shown in FIG. 7B, which are located seven pitches ahead of the positions of FIG. 7A, with respect to the direction of arrow Y.

For example, reaction tube 111a is observed attentively with every cycle of rotation, to follow up the rotational positions to which reaction tubes 111a to 111m are moved. FIG. 8 shows the result of such observation. In FIG. 8, (1) corresponds to the stop position of reaction tube 111a in FIG. 7A, and (2) indicates a stop position reached after one cycle of rotation for 7-pitch movement. Likewise, (3) to (13) indicate stop positions reached after the following individual cycles of rotation. This result applies also to all of 12 other reaction tubes 111b to 111m, except for the first stop position.

In consideration of the aforementioned stop positions of reaction tubes 111a to 111m, washing unit 115, sample dispensing unit 116, first stirring unit 117, second-reagent dispensing unit 118, first-reagent dispensing unit 119, and second stirring unit 120 are arranged around ring-shaped holder 113 in the order named. In the stop state of FIG. 7A, washing positions A are set at the stop positions of reaction tubes 111b, 111c and 111d; sample dispensing position B at the stop position of tube 111a, first stirring position D at the stop position of tube 111m, second-reagent dispensing position E at the stop position of tube 111l, first-reagent dispensing position C at the stop position of tube 111g, and second stirring position F at the stop position of tube 111e. In these individual positions, specified operations of the analyzer are performed for reaction tubes 111a to 111m. As shown in FIG. 6, washing unit 115 includes washing nozzles 115a, e.g., three in number, which serve to wash their corresponding reaction tubes 111b, 111c and 111d at washing positions A. Sample dispensing unit 16 includes a plurality of sample vessels 116a each containing a sample, rotatable sample holder 116b holding vessels 116a, and sampling nozzle 116c. Nozzle 116c serves to such a sample from a specified one of vessels 116a held by holder 116b, and dispense it to reaction tube 111a at sample dispensing position B. First-reagent dispensing unit 119 includes a plurality of first-reagent vessels 119a containing a first reagent, rotatable first-reagent holder 119b holding vessels 119b, and first-reagent dispensing nozzle 119c. Nozzle 119c serves to suck the first reagent from a specified one of vessels 119a held by holder 119b, and dispense it to reaction tube 11g at first-reagent dispensing position C. First stirring unit 117 includes first stirrer 117a for stirring the contents of reaction tube 111m at first stirring position D. Second-reagent dispensing unit 118 includes a plurality of second-reagent vessels 118a containing a second reagent, rotatable second-reagent holder 118b holding vessels 118a, and second-reagent dispensing nozzle 118c. Nozzle 118c serves to suck the second reagent from a specified one of vessels 118a held by holder 118b, and dispense it to reaction tube 111l at second-reagent dispensing position E. Second stirring unit 120 includes second stirrer 120a for stirring the contents of reaction tube 11e at second stirring position F.

Numeral 121 denotes a thermostatic unit which keeps reaction tubes 111a to 111m, held by holder 113 on rotating table 111, at a fixed temperature, e.g., 37° C.

Numeral 122 denotes a photometric system, which includes light source 123 and light sensing element 24. Light emitted from light source 23 crosses the path of transfer of reaction tubes 111a to 111m, and is received by sensing element 124. When moving tubes 111a to 111m intercept the light emitted from source 123 toward element 124, the rates of quantity or intensity of light transmitted through tubes 111a to 111m vary, depending on the contents of the tubes. Thus, sensing element 124 detects, as photometric data, absorbances corresponding to the rates of light quantity.

An output signal from light sensing element 124 is converted into a digital signal by A/D converter 125, and is supplied to CPU 126. Display 127, printer 128, and control panel 129 are connected to CPU 126. By operation on control panel 129, a measurement result can be indicated on display 127, and printer 128 can be started for a print-out.

Figure 7A:
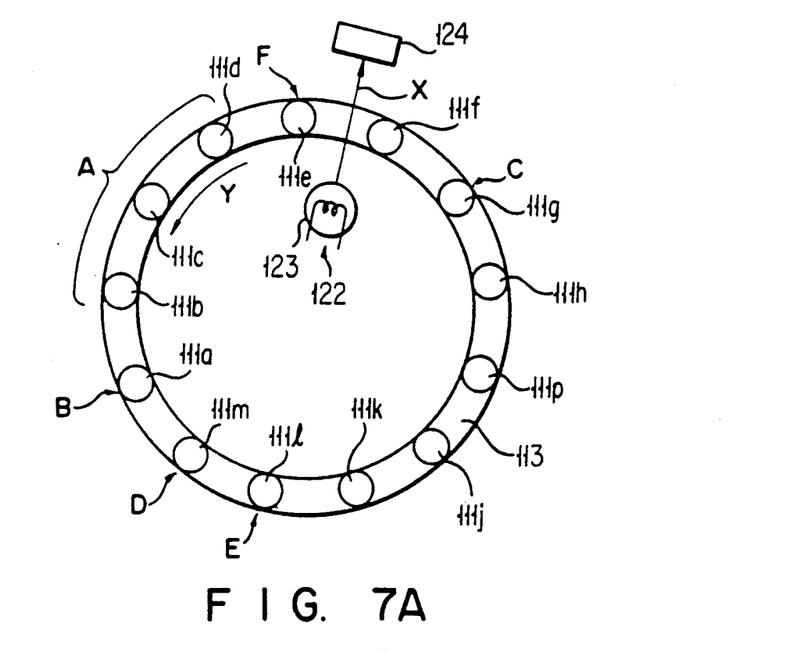
FIGS. 7A and 7B are diagrams illustrating the operating principle of the analyzer shown in FIG. 6.
Figure 7B:
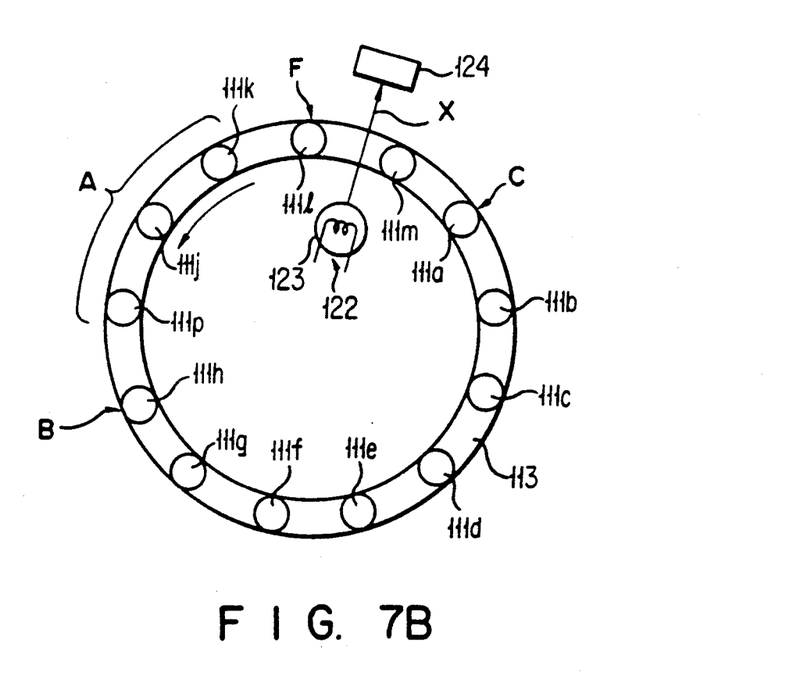
Figure 8:
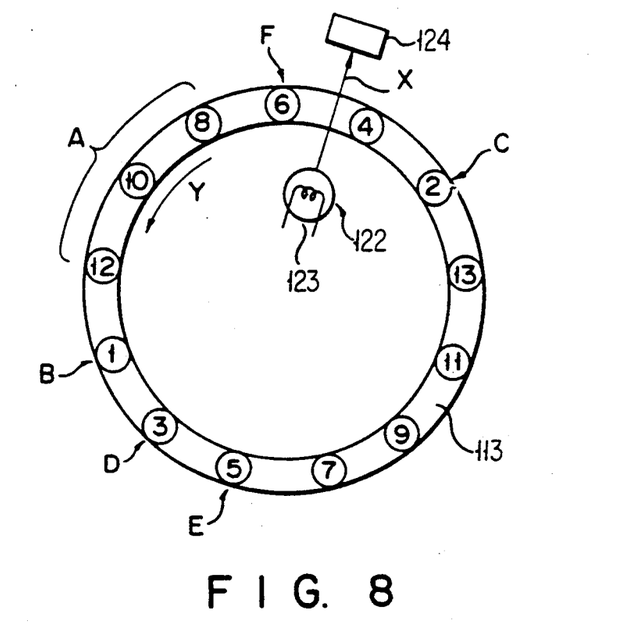
FIG. 8 is a diagram for illustrating stop positions of tubes used in the analyzer shown in FIG. 6.

In the stop state of FIG. 7A, reaction tubes 111b, 111c and 111d are washed at washing positions A. Thus, samples (e.g., serum) and reagents, dispensed to and mixed in the reaction tubes before reaching washing positions A, are washed away. In sample dispensing position B, a sample is dispensed to reaction tube 111a having been washed at washing positions A in the last cycle but one. In first-reagent dispensing position C, the first reagent is dispensed to reaction tube 111g having been injected with a sample in sample dispensing position B in the last cycle. In first stirring position D, a sample and the first reagent in reaction tube 111m, having been injected with the first reagent in first-reagent dispensing position C in the last cycle, are stirred. In second-reagent dispensing position E, the second reagent is dispensed to reaction tube 111l, having had a sample and the first reagent stirred therein in the last cycle but one. In second stirring position F, a sample and the first and second reagents in reaction tube 111e, having been injected with the second reagent in the last cycle, are stirred.

After the stop state of FIG. 7A is maintained for a predetermined period of time, ring-shaped holder 113 is rotated in the direction of arrow Y for another predetermined period of time. After moving reaction tubes 111a to 111m in this manner, holder 113 is stopped at the position of FIG. 7B. During such movement, reaction tubes 111a to 111m enjoy a continuous photometric process. In the stop state of FIG. 7B, specified operations are performed for tubes 111a to 111m in their respective positions, just as in the stop state of FIG. 7A.

According to the arrangement described above, each of reaction tubes 111a to 111m moves substantially half round the arrangement line in one cycle. Thus, the time required for the movement of tubes 111a to 111m during each cycle, and therefore, one cycle time, can be shortened.

Reaction tubes 111a to 111m are arranged substantially regularly with the progress of reaction (in the order of the size of position number). When the reaction tubes at positions (8) to (13) are to be washed, for example, (8), (10) and (12) constitute one closely-situated group, and (9), (11) and (13) constitute another. In this manner, washing positions A can be situated collectively in specific continuous regions around holder 13.

Thus, the structural space for the analyzer can be utilized effectively, so that the analyzer can be improved in compactness.

Figure 9:
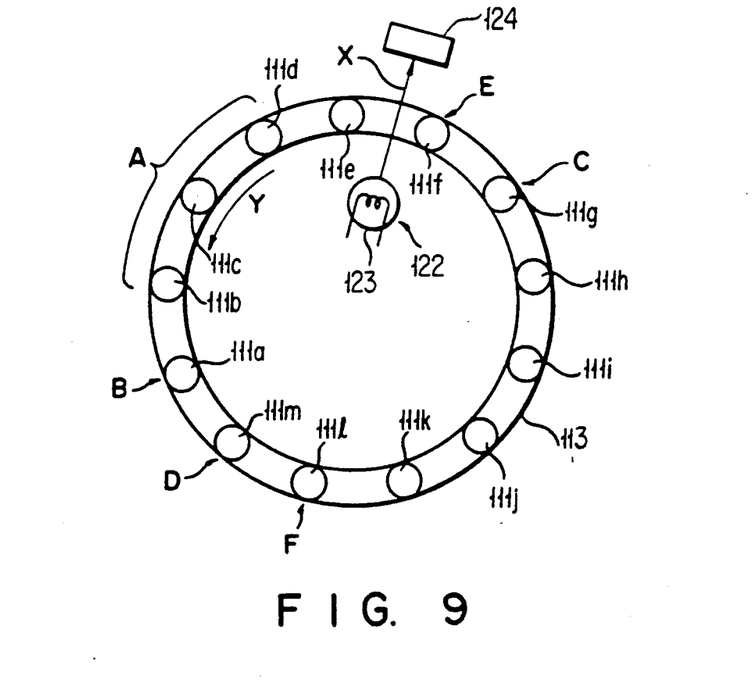
FIG. 9 shows a modification of the analyzer of FIG. 6, in which a second-reagent dispensing position and a second stirring position are changed.

Moreover, first and second stirring positions D and F can be brought closer to each other by shifting second-reagent dispensing position E and position F in the manner shown in FIG. 9. Accordingly, first and second stirring operations can be accomplished with use of only one stirring unit.

Figure 10:
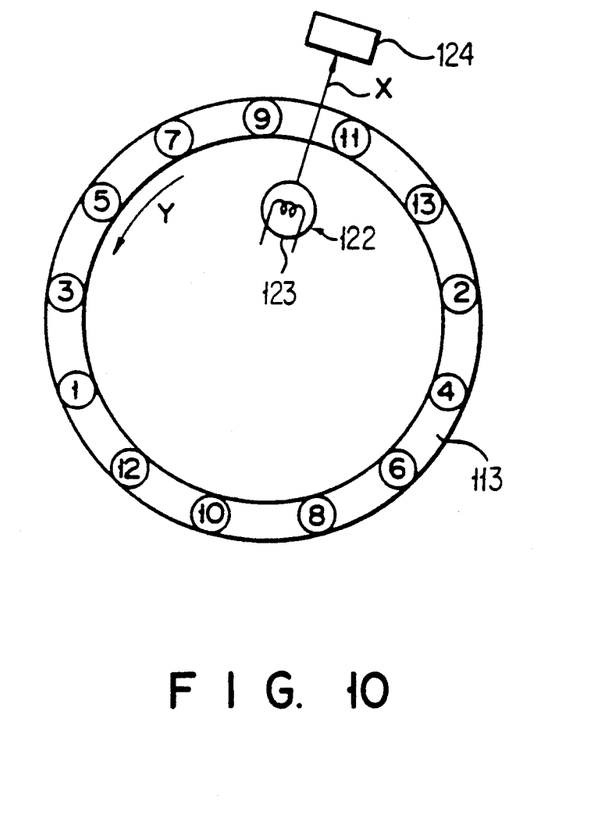
FIG. 10 shows a modification of the analyzer of FIG. 6, in which the stop positions are changed.

In the embodiment described above, each reaction tube is transferred to the first stop position it reaches after having moved half round circular arrangement line 114, in each cycle. In other words, number P of pitches covered in each cycle is $(n+1)/2$. The present invention is not, however, limited to such an arrangement. For example, each reaction tube may be transferred, in each cycle, to the last stop position it reached while moving half round line 114. In this case, pitch number P for each cycle is $(n-1)/2$, and reaction tubes 11a to 11m move in the order shown in FIG. 10.

Moreover, the present invention may be arrangement so that reaction tubes 111a to 111m make substantially one and a half or two and a half or three and a half revolutions along arrangement line 114, for each cycle. In short, the arrangement of the invention must only be such that the first stop position for each reaction tube is situated at a distance corresponding to a substantially half revolution, along the arrangement line, from the second stop position next thereto. Thus, it is necessary only that the distance between the first and second stop positions be $\{(m-1)n+(n\pm1)/2\}$ pitches, where m is a natural number, n is the number of reaction tubes, and one pitch is defined as the interval between each two adjacent reaction tubes. Furthermore, the washing positions may alternatively be situated at positions A' of FIG. 8.

What is claimed is:

1. A method for performing automatic chemical analysis, comprising:

provinding $(2L+1)$ reaction tubes for holding a chemical solution to be reacted, where L is an integer;

supporting said $(2L+1)$ reaction tubes in a loop;

forwarding predetermined odd multiples of L or $L+1$ reaction tubes past a predetermined location in said loop and stopping for a predetermined interval;

photometrically measuring the solution of the tubes passing by a predetermined location during forward of said reaction tubes; and, washing the reaction tubes during stopping for said predetermined interval.

2. The method according to claim 1, wherein said photometrically measuring step comprises subjecting the moving reaction tubes to a continuous photometric process.

* * * * *